US011053548B2

(12) United States Patent
Gore

(10) Patent No.: US 11,053,548 B2
(45) Date of Patent: Jul. 6, 2021

(54) METHODS FOR DETECTING ANEUPLOIDY

(71) Applicant: GOOD START GENETICS, INC, Cambridge, MA (US)

(72) Inventor: Athurva Gore, Cambridge, MA (US)

(73) Assignee: Good Start Genetics, Inc., Cambridge, MA (US)

( * ) Notice: Subject to any disclaimer, the term of this patent is extended or adjusted under 35 U.S.C. 154(b) by 752 days.

(21) Appl. No.: 14/710,229

(22) Filed: May 12, 2015

(65) Prior Publication Data

US 2015/0322524 A1    Nov. 12, 2015

Related U.S. Application Data

(60) Provisional application No. 61/991,839, filed on May 12, 2014.

(51) Int. Cl.
C12Q 1/6883 (2018.01)
C12Q 1/6827 (2018.01)
C12Q 1/6809 (2018.01)
G16B 20/00 (2019.01)

(52) U.S. Cl.
CPC ......... *C12Q 1/6883* (2013.01); *C12Q 1/6809* (2013.01); *C12Q 1/6827* (2013.01); *G16B 20/00* (2019.02); *C12Q 2600/156* (2013.01)

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,988,617 | A | 1/1991 | Landegren et al. |
| 5,060,980 | A | 10/1991 | Johnson et al. |
| 5,210,015 | A | 5/1993 | Gelfand et al. |
| 5,234,809 | A | 8/1993 | Boom et al. |
| 5,242,794 | A | 9/1993 | Whiteley et al. |
| 5,348,853 | A | 9/1994 | Wang et al. |
| 5,459,307 | A | 10/1995 | Klotz, Jr. |
| 5,486,686 | A | 1/1996 | Zdybel, Jr. et al. |
| 5,494,810 | A | 2/1996 | Barany et al. |
| 5,567,583 | A | 10/1996 | Wang et al. |
| 5,583,024 | A | 12/1996 | McElroy et al. |
| 5,604,097 | A | 2/1997 | Brenner |
| 5,636,400 | A | 6/1997 | Young |
| 5,674,713 | A | 10/1997 | McElroy et al. |
| 5,695,934 | A | 12/1997 | Brenner |
| 5,700,673 | A | 12/1997 | McElroy et al. |
| 5,701,256 | A | 12/1997 | Marr et al. |
| 5,830,064 | A | 11/1998 | Bradish et al. |
| 5,846,719 | A | 12/1998 | Brenner et al. |
| 5,863,722 | A | 1/1999 | Brenner |
| 5,866,337 | A | 2/1999 | Schon |
| 5,869,252 | A | 2/1999 | Bouma et al. |
| 5,869,717 | A | 2/1999 | Frame et al. |
| 5,871,921 | A | 2/1999 | Landegren et al. |
| 5,888,788 | A | 3/1999 | De Miniac |
| 5,942,391 | A | 8/1999 | Zhang et al. |
| 5,971,921 | A | 10/1999 | Timbel |
| 5,993,611 | A | 11/1999 | Moroney, III et al. |
| 5,994,056 | A | 11/1999 | Higuchi |
| 6,033,854 | A | 3/2000 | Kumit et al. |
| 6,033,872 | A | 3/2000 | Bergsma et al. |
| 6,100,099 | A | 8/2000 | Gordon et al. |
| 6,138,077 | A | 10/2000 | Brenner |
| 6,150,516 | A | 11/2000 | Brenner et al. |
| 6,171,785 | B1 | 1/2001 | Higuchi |
| 6,172,214 | B1 | 1/2001 | Brenner |
| 6,172,218 | B1 | 1/2001 | Brenner |
| 6,197,508 | B1 | 3/2001 | Stanley |
| 6,197,574 | B1 | 3/2001 | Miyamoto et al. |
| 6,210,891 | B1 | 4/2001 | Nyren et al. |
| 6,223,128 | B1 | 4/2001 | Allex et al. |
| 6,235,472 | B1 | 5/2001 | Landegren et al. |
| 6,235,475 | B1 | 5/2001 | Brenner et al. |

(Continued)

FOREIGN PATENT DOCUMENTS

| EP | 1 321 477 A1 | 6/2003 |
| EP | 1 564 306 A2 | 8/2005 |

(Continued)

OTHER PUBLICATIONS

Xie et al, CNV-seq, a new method to detect copy number variation using high-throughput sequencing BMC Bioinformatics 2009; available from: http://www.biomedcentral.com/1471-2105/10/80.*

Fiorentino et al, Development and validation of a next-generation sequencing-based protocol for 24-chromosome aneuploidy screening of embryos vol. 101, Issue 5, pp. 1375-1382.e2; DOI: https://doi.org/10.1016/j.fertnstert.2014.01.051.*

Sargent, 1988, Isolation of differentially expressed genes, Methods Enzymol 152:423-432.

Sauro, 2004, How Do You Calculate a Z-Score/ Sigma Level?, https://www.measuringusability.com/zcalc.htm (online publication).

(Continued)

*Primary Examiner* — Joseph Woitach

(74) *Attorney, Agent, or Firm* — Sterne, Kessler, Goldstein & Fox P.L.L.C.

(57) ABSTRACT

The invention generally relates to methods for determining aneuploidy of cells with respect to a control sample. In certain embodiments, the method involves exposing a sample to a plurality of probes capable of capturing DNA from at least one chromosome suspected of having an altered copy number, and at least one control DNA sample known or suspected to have a stable copy number, capturing and sequencing DNA that binds to the probes, calculating a chromosomal read fraction; determining a sample specific scaling factor; scaling the chromosomal read fractions, normalizing the scaled read fractions, and determining a copy number state of at least one chromosome.

11 Claims, 3 Drawing Sheets

(56) References Cited

U.S. PATENT DOCUMENTS

| | | |
|---|---|---|
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vemachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugham, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugham, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0091666 A1 | 7/2002 | Rice et al. |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0106112 A1 | 6/2004 | Nilsson et al. |
| 2004/0142325 A1 | 7/2004 | Mintz et al. |
| 2004/0152108 A1 | 8/2004 | Keith et al. |
| 2004/0170965 A1 | 9/2004 | Scholl et al. |
| 2004/0171051 A1 | 9/2004 | Holloway |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0272065 A1 | 12/2005 | Lakey et al. |
| 2006/0019304 A1 | 1/2006 | Hardenbol et al. |
| 2006/0024681 A1 | 2/2006 | Smith et al. |
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0292585 A1 | 12/2006 | Nautiyal et al. |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0176209 A1 | 7/2008 | Muller et al. |

(56) References Cited

U.S. PATENT DOCUMENTS

| | | |
|---|---|---|
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2013/0130921 A1 | 5/2013 | Gao et al. |
| 2013/0178378 A1 | 7/2013 | Hatch et al. |
| 2013/0183672 A1 | 7/2013 | de Laat et al. |
| 2013/0222388 A1 | 8/2013 | McDonald |
| 2013/0268474 A1 | 10/2013 | Nizzari et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0318274 A1 | 10/2014 | Zimmerman et al. |
| 2014/0361022 A1 | 12/2014 | Finneran |
| 2015/0056613 A1 | 2/2015 | Kural |
| 2015/0178445 A1 | 6/2015 | Cibulskis et al. |
| 2015/0299767 A1 | 10/2015 | Armour et al. |
| 2016/0034638 A1 | 2/2016 | Spence et al. |
| 2016/0210486 A1 | 7/2016 | Porreca et al. |
| 2017/0129964 A1 | 5/2017 | Cheung |

FOREIGN PATENT DOCUMENTS

| | | |
|---|---|---|
| EP | 2 437 191 A2 | 4/2012 |
| EP | 2425240 A4 | 12/2012 |
| EP | 2716766 A1 | 4/2014 |
| WO | 95/011995 A1 | 5/1995 |
| WO | 96/019586 A1 | 6/1996 |
| WO | 98/014275 A1 | 4/1998 |
| WO | 98/044151 A1 | 10/1998 |
| WO | 00/018957 A1 | 4/2000 |
| WO | 02/093453 A2 | 11/2002 |
| WO | 2004/018497 A2 | 3/2004 |
| WO | 2004/083819 A2 | 9/2004 |
| WO | 2005/003304 A2 | 1/2005 |
| WO | 2007/010251 A2 | 1/2007 |
| WO | 2007/107717 A1 | 9/2007 |
| WO | 2007/123744 A2 | 11/2007 |
| WO | 2007/135368 A2 | 11/2007 |
| WO | 2008067551 A2 | 6/2008 |
| WO | 2009/036525 A2 | 3/2009 |
| WO | 2010/024894 A1 | 3/2010 |
| WO | 2010/126614 A2 | 11/2010 |
| WO | 2011/102998 A2 | 8/2011 |
| WO | 2012/006291 A2 | 1/2012 |
| WO | 2012/040387 A1 | 3/2012 |
| WO | 2012/051208 A2 | 4/2012 |
| WO | 2012/087736 A1 | 6/2012 |
| WO | 2012/109500 A2 | 8/2012 |
| WO | 2012/134884 A1 | 10/2012 |
| WO | 2013/058907 A1 | 4/2013 |
| WO | 2013/148496 A1 | 10/2013 |
| WO | 2013/177086 A1 | 11/2013 |
| WO | 2013/191775 A2 | 12/2013 |
| WO | 2014/074246 A1 | 5/2014 |

OTHER PUBLICATIONS

Sauro, 2004, What's a Z-Score and Why Use it in Usability Testing?, https://www.measuringusability.com/z.htm (online publication).

Schadt, 2010, A window into third-generation sequencing, Human Mol Genet 19(R2):R227-40.

Schatz et al., 2010, Assembly of large genomes using second-generation sequencing, Genome Res., 20:1165-1173.

(56) References Cited

OTHER PUBLICATIONS

Schiffman, 2009, Molecular inversion probes reveal patterns of 9p21 deletion and copy number aberrations in childhood leukemia, Cancer Genetics and Cytogenetics 193:9-18.
Schneeberger, 2011, Reference-guided assembly of four diverse *Arabidopsis thaliana* genomes, PNAS 108 (25):10249-10254.
Schouten, 2002, Relative Quantification of 40 Nucleic Acid Sequences by Multiplex Ligation-Dependent Probe Amplification, Nude Acids Res 30 (12):257.
Schrijver, 2005, Diagnostic testing by CFTR gene mutation analysis in a large group of Hispanics, J Mol Diag 7 (2):289-299.
Schuette et al., 1995, Sequence analysis of phosphorothioate oligonucleotides via matrix-assisted laser desorption ionization time-of-flight mass spectrometry, J. Pharm. Biomed. Anal 13:1195-1203.
Schwartz et al., 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31.
Smirnov, 1996, Sequencing oligonucleotides by exonuclease digestion and delayed extraction matrix-assisted laser desorption ionization time-of-flight mass spectrometry, Anal Biochem 238:19-25.
Smith, 1985, The synthesis of oligonucleotides containing an aliphatic amino group at the 5' terminus: synthesis of fluorescent DNA primers for use in DNA sequence analysis, Nucl. Acid Res., 13:2399-2412.
Smith, 2010, Highly-multiplexed barcode sequencing: an efficient method for parallel analysis of pooled samples, Nucleic Acids Research 38(13):e142 (8 pages).
Soni, 2007, Progress toward ultrafast DNA sequencing using solid-state nanopores, Clin Chem 53(11):1996-2001.
Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxyribonucleotides, Nucl Acid Res 15:4837-4848.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30)1-9.
Thauvin-Robinet, 2009, The very low penetrance of cystic fibrosis for the R117H mutation: a reappraisal for genetic ,munseling and newborn screening, J Med Genet 46:752-758.
Thiyagarajan, 2006, PathogenMIPer: a tool for the design of molecular inversion probes to detect multiple pathogens, BMC Bioinformatics 7:500.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tkachuk, 1990, Detection of bcr-abl Fusion in Chronic Myelogeneous Leukemia by in Situ Hybridization, Science 250:559.
Tobler, 2005, The SNPlex Genotyping System: A Flexible and Scalable Platform for SNP Genotyping, J Biomol Tech 16(4):398.
Tokino, 1996, Characterization of the human p57 KIP2 gene: alternative splicing, insertion/deletion polymorphisms in VNTR sequences in the coding region, and mutational analysis, Human Genetics 96:625-31.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013.
Umbarger, 2014, Next-generation carrier screening, Gen Med 16(2):132-140.
Veeneman, 2012, Oculus: faster sequence alignment by streaming read compression, BMC Bioinformatics 13:297.
Wallace 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.
Wang et al., 2005, Allele quantification using molecular inversion probes (MIP), Nucleic Acids Research 33(21):e183.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988.
Watson et al., 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162.
Kircher, 2010, High-througput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLoS One 6(8):e23455.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2):219-229.
Krishnakumar, 2008, A comprehensive assay for targeted multiplex amplification of human DNA sequences, PNAS 105:9296-301.

(56) References Cited

OTHER PUBLICATIONS

Kumar, 2010, Comparing de novo assemblers for 454 transcriptome data, Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.
Li, 2003, DNA binding and cleavage by the periplasmic nuclease Vvn: a novel structure with a known active site, EMBO J 22(15):4014-4025.
Li, 2008, SOAP: short oligonucleotide alignment program, Bioinformatics 24(5):713-14.
Li, 2009, Fast and accurate short read alignment with Burrows-Wheeler transform, Bioinformatics, 25 (14):1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, Fast and accurate long-read alignment with Burrows-Wheeler transform, Bioinformatics 26(5):589-95.
Li, 2011, Improving SNP discovery by base alignment quality, Bioinformatics 27:1157.
Li, 2011, Single nucleotide polymorphism genotyping and point mutation detection by ligation on microarrays, J Nanosci Nanotechnol 11(2):994-1003.
Li, 2012, A new approach to detecting low-level mutations in next-generation sequence data, Genome Biol 13:1-15.
Li, 2014, HUGO: Hierarchical mUlti-reference Genome cOmpression for aligned reads, JAMIA 21:363-373.
Lin, 2008, ZOOM! Zillions of Oligos Mapped, Bioinformatics 24:2431.
Lin, 2010, A molecular inversion prove assay for detecting alternative splicing, BMC Genomics 11(712):1-14.
Lin, et al., 2012, Development and evaluation of a reverse dot blot assay for the simultaneous detection of common alpha and beta thalassemia in Chinese, Blood Cells Molecules, and Diseases 48(2):86-90.
Lipman et al., 1985, Rapid and sensitive protein similarity searches, Science 227(4693):1435-41.
Liu et al., 2012, Comparison of next-generation sequencing systems, ePub 2012(251364).
Llopis, 1998, Measurement of cytosolic, mitochondrial, and Golgi pH in single living cells with green fluorescent proteins, PNAS 95(12):6803-08.
Ma, 2006, Application of real-time polymerase chain reaction (RT-PCR), J Am Soc 1-15.
MacArthur, 2014, Guidelines for investigating causality of sequence variants in human disease, Nature 508:469-76.
Maddalena, 2005, Technical standards and guidelines: molecular genetic testing for ultra-rare disorders, Genet Med 7:571-83.
Malewicz, 2010, Pregel: a system for large-scale graph processing, Proc. ACM SIGMOD Int Conf Mgmt Data 135-46.
Mamanova, 2010, Target-enrichment strategies for nextgeneration sequencing, Nature Methods 7(2):111-8.
Margulies, 2005, Genome sequencing in micro-fabricated high-density picotiter reactors, Nature, 437:376-380.
Marras 1999, Multiplex detection of single-nucleotide variations using molecular beacons, Genetic Analysis: Biomolecular Engineering 14:151.
Maxam, 1977, A new method for sequencing DNA, PNAS 74:560-564.
May, 1988, How Many Species Are There on Earth?, Science 241(4872):1441-9.

McDonnell, "Antisepsis, disinfection, and sterilization: types, action, and resistance," p. 239 (2007).
McKenna, 2010, The Genome Analysis Toolkit: a MapReduce framework for analyzing next-generation DNA sequencing data, Genome Res 20(9):1297-1303.
Meyer, 2007, Targeted high-throughput sequencing of tagged nucleic acid samples, Nucleic Acids Research 35(15):e97 (5 pages).
Meyer, 2008, Parallel tagged sequencing on the 454 platform, Nature Protocols 3(2):267-78.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32(17):e135.
Minton, 2011, Mutation Surveyor: software for DNA sequence analysis, Meth Mol Biol 688:143-53.
Adey, 2010, Rapid, low-input, low-bias construction of shotgun fragment libraries by high-density in vitro transposition, Genome Biol 11:R119.
Ageno, 1969, The alkaline denaturation of DNA, Biophys J 9(11):1281-1311.
Agrawal, 1990, Site-specific functionalization of oligodeoxynucleotides for non-radioactive labelling, Tetrahedron Let 31:1543-1546.
Akhras, 2007, Connector Inversion Probe Technology: A Powerful OnePrimer Multiplex DNA Amplification System for Numerous Scientific Applications PLOS ONE 2(9):e915.
Alazard, 2002, Sequencing of production-scale synthetic oligonucleotides by enriching for coupling failures using matrix-assisted laser desorption/ionization time-of-flight mass spectrometry, Anal Biochem 301:57-64.
Alazard, 2006, Sequencing oligonucleotides by enrichment of coupling failures using matrix-assisted laser desorption/ionization time-of-flight mass spectrometry, Curr Protoc Nucleic Acid Chem, Chapter 10, Unit 10:1-7.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401.
Ball et al., 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau et al., 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carver testing for severe childhood recessive diseases by next-generation sequencing, Sci Trans Med 3 (65ra4).
Benner, 2001, Evolution, language and analogy in functional genomics, Trends Genet 17:414-8.
Bentzley et al., 1998, Base specificity of oligonucleotide digestion by calf spleen phosphodiesterase with matrix-assisted laser desorption ionization analysis, Anal Biochem 258:31-37.
Bentzley, 1996, Oligonucleotide sequence and composition determined by matrix-assisted laser desorption/ionization, Anal Chem 68:2141-2146.

(56) References Cited

OTHER PUBLICATIONS

Bickle & Kruger, 1993, Biology of DNA Restriction, Microbiol Rev 57(2):434-50.
Bonfield, 2013, Compression of FASTQ and SAM format sequencing data, PLoS One 8(3):e59190.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslaysky, 2003, Sequence information can be obtained from single DNA molecules, PNAS 100:3960-4.
Brinkman, 2004, Splice Variants as Cancer Biomarkers, Clin Biochem 37:584.
Brown et al., 1979, Chemical synthesis and cloning of a tyrosine tRNA gene, Methods Enzymol 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.
Chan, 2011, Natural and engineered nicking endonucleases—from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013.
Chevreux, 1999, Genome sequence assembly using trace signals and additional sequence information, Proc GCB 99:45-56.
Chirgwin et al., 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Ciotti, 2004, Triplet repeat prmied PCR (TP PCR) in molecular diagnostic testing for Friedrich ataxia, J Mol Diag 6(4):285-9.
Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355.
Cronin, 1996, Cystic Fibrosis Mutation Detection by Hybridization to Light-Generated DNA Probe Arrays Human Mutation 7:244.
Dahl et al., 2005, Multiplex amplification enabled by selective circularization of large sets of genomic DNA fragments, Nucleic Acids Res 33(8):e71.
Danecek, 2011, The variant call format and VCFtools, Bioinformatics 27(15):2156-2158.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, DELIMINATE—a fast and efficient methods for loss-less compression of genomice sequences, Bioinformatics 28(19):2527-2529.
Moudrianakis, 1965, Base sequence determination in nucleic acids with the electron microscope, III. Chemistry and microscopy of guanine-labeled DNA, PNAS 53:564-71.
Mullan, 2002, Multiple sequence alignment—the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nilsson et al., 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Owens 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130.

(56) References Cited

OTHER PUBLICATIONS

Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.
Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplification of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed. (72 pages).
Quail, 2010, DNA: Mechanical Breakage, In Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS ONE 3:e3373.
Roberts, 1980, Restriction and modification enzymes and their recognition sequences, Nucleic Acids Res 8(1):r63-r80.
Robinson et al., 2013, Graph Databases, O'Reilly Media, Inc., Sebastopol, CA (223 pages).
Rodriguez, 2010, Constructions from Dots and Lines, Bull Am Soc Int Sci Tech 36(6):35-41.
Rosendahl et al., 2013, CFTR, SPINKI, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Saihan, 2009, Update on Usher syndrome, Cur Op Neurology 22:19-27.
Sanger et al., 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial tRNAphe Variant m.593T.Ca Synergistically Pathogenic Mutation in Chinese LHON Families with m.11778G.A? PLoS ONE 6(10):e26511.
Zhao, 2009, PGA4genomics for comparative genome assembly based on genetic algorithm optimization, Genomics 94 (4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30 (8):1073-1080.
Zimmerman, 2010, A novel custom resequencing array for dilated cardiomyopathy, Gen Med 12(5):268-78.
Zuckerman, 1987, Efficient methods for attachment of thiol specific probes to the 3'-ends of synthetic oligodeoxyribonucleotides, Nucl Acid Res 15(13):5305-5321.
Husemann, 2009, Phylogenetic Comparative Assembly, Algorithms in Bioinformatics: 9th International Workshop, pp. 145-156, Salzberg & Warnow, Eds. Springer-Verlag, Berlin, Heidelberg.
Illumina, 2010, De Novo assembly using Illumina reads, Technical Note (8 pages).
International Human Genome Sequencing Consortium, 2004, Finishing the euchromatic sequence of the human genome, Nature 431:931-945.
International Search Report and Written Opinion dated Dec. 2, 2015, for International Patent Application No. PCT/US2015/049132 with Internaional Filing Date Sep. 9, 2015 (14 pages).
Iqbal, 2012, De novo assembly and genotyping of variants using colored de Bruijn graphs, Nature Genetics 44:226-232.
Isosomppi, 2009, Disease-causing mutations in the CLRN1 gene alter normal CLRN1 protein trafficking to the plasma membrane, Mol Vis 15:1806-1818.
Jaijo et al., 2010, Microarray-based mutation analysis of 183 Spanish families with Usher syndrome, Invest Ophthalmol Vis Sci 51(3):1311-7.
Jensen, 2001, Orthologs and paralogs—we need to get it right, Genome Biol 2(8):1002-1002.3.
Jones et al., 2008, Core Signaling Pathways in Human Pancreatic Cancers Revealed by Global Genomic Analyses, Science 321(5897):1801-1806.
Kambara et al., Optimization of Parameters in a DNA Sequenator Using Fluorescence Detection, Nature Biotechnology 6:816-821 (1988).
Kennedy et al., 2013, Accessing more human genetic variation with short sequencing reads, American Society of Human Genetics 63rd Annual Meeting, Abstract, Oct. 22, 2013.
Kent, 2002, BLAT—The BLAST-like alignment tool, Genome Res 12(4): 656-664.
De la Bastide, 2007, Assembling genome DNA sequences with PHRAP, Current Protocols in Bioinformatics 17:11.4.1-11.4.15.

(56) References Cited

OTHER PUBLICATIONS

Delcher et al., 1999, Alignment of whole genomes, Nuc Acids Res 27(11):2369-2376.
Den Dunnen, 2003, Mutation Nomenclature, Curr Prot Hum Genet 7.13.1-7.13.8.
Deng et al., 2009, Targeted bisulfite sequencing reveals changes in DNA methylation associated with nuclear reprogramming, nature biotechnology 27:353-60 (and supplement).
Deng et. al., 2012, Supplementary Material, Nature Biotechnology, S1-1-S1-1 1, Retrieved from the Internet on Oct. 24, 2012.
Deorowicz, 2013, Data compression for sequencing data, Alg for Mole Bio 8:25.
Diep et al., 2012, Library-free methylation sequencing with bisulfite padlock probes, Nature Methods 9:270-272 (and supplemental information).
DiGuistini et al., 2009, De novo sequence assembly of a filamentous fungus using Sanger, 454 and Illumina sequence lata, Genome Biology, 10:R94.
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Dong & Yu, 2011, Mutation surveyor: An in silico tool for sequencing analysis, Methods Mol Biol 760:223-37.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12):e1000589.
Ericsson, 2008, A dual-tag microarray platform for high-performance nucleic acid and protein analyses, Nucl Acids Res 36:e45.
Fares, et al., 2008, Carrier frequency of autosomal-recessive disorders in the Ashkenazi Jewish population: should the rationale for mutation choice for screening be reevaluated?, Prenatal Diagnosis 28:236-41.
Faulstich et al., 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014.
Fitch, 1970, Distinguishing homologs from analogous proteins, Syst Biol 19(2):99-113.
Flaschker et al., 2007, Description of the mutations in 15 subjects with variant forms of maple syrup urine disease, J Inherit Metab Dis 30:903-909.
Frey, Bruce, 2006, Statistics Hacks 108-115.
Friedenson, 2005, BRCA1 and BRCA2 Pathways and the Risk of Cancers Other Than Breast or Ovarian, Medscape General Medicine 7(2):60.
Furtado et al., 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Garber, 2008, Fixing the front end, Nature Biotechnology 26(10):1101-04.
Gemayel et al., 2010, Variable Tandem Repeats Accelerate Evolution of Coding and Regulatory Sequences, Annual Review of Genetics 44:445-77.
Giusti, 1993, Synthesis and Characterization of f'-Fluorescent-dye-labeled Oligonucleotides, PCR Meth Appl 2:223-227.
Glover et al., 1995, Sequencing of oligonucleotides using high performance liquid chromatography and electrospray mass spectrometry, Rapid Com Mass Spec 9:897-901.
Gnirke et al., 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan (106 pages).
Goto, 2010, BioRuby: bioinformatics software for the Ruby programming language, Bioinformatics 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nucl Acids Res 19(11):3019-3025.
Gustincich et al., 1991, A fast method for high-quality genomic DNA extraction from whole human blood, BioTechniques 11(3):298-302.
Gut, 2995, A procedure for selective DNA alkylation and detection by mass spectrometry, Nucl Acids Res 23(8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harris, 2006, Defects can increase the melting temperature of DNA-nanoparticle assemblies, J Phys Chem B 110(33):16393-6.
Harris, 2008, Single-molecule DNA sequencing of a viral genome, Science 320(5872):106-9.
Harris, 2008, Helicos True Single Molecule Sequencing (tSMS) Science 320:106-109.
Heger, 2006, Protonation of Cresol Red in Acidic Aqueous Solutions Caused by Freezing, J Phys Chem B 110(3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer et al., 2008, Resolving Individuals Contributing Trace Amounts of DNA to Highly Complex Mixtures Using High-Density SNP Genotyping Microarrays. PLoS One 4(8):e1000167.
Homer, 2009, BFAST: An alignment tool for large scale genome resequencing, PLoS ONE 4(11):e7767.
Housley, 2009, SNP discovery and haplotype analysis in the segmentally duplicated DRD5 coding region, Ann Hum Genet 73(3):274-282.
Huang, 2008, Comparative analysis of common CFTR polymorphisms poly-T, TGrepeats and M470V in a healthy Chinese population, World J Gastroenterol 14(12):1925-30.

\* cited by examiner

METHODS FOR DETECTING ANEUPLOIDY

RELATED APPLICATIONS

This application claims the benefit of and priority to U.S. provisional application 61/991,839 filed May 12, 2014, the contents of which are incorporated by reference.

FIELD OF THE INVENTION

The present invention relates to the field of diagnosis of fetal aneuploidy.

BACKGROUND

A woman undergoing in-vitro fertilization (IVF) may require the implantation of several embryos or multiple successive implantation procedures. To increase the chances of a full term pregnancy resulting from IVF, pre-implantation genetic screening (PGS), which assesses the chromosome copy number of the embryo, is employed for the detection of possible birth defects. Common birth defect may be caused by an abnormal number of chromosomes. Identification and exclusion of embryos containing such possible birth defects increases the likelihood of a resulting pregnancy.

Detection of aneuploidy in embryos prior to embryo transfer reduces implantation failures and spontaneous miscarriages after IVF. The majority of aneuploidy conditions, such as trisomy and monosomy, are lethal to the fetus and cause spontaneous abortions or death immediately after birth. Down's syndrome, trisomy 21, is the most common and most serious congenital abnormality found at birth, with a prevalence of one in 660 live births. Approximately a third of all fetuses with Down's syndrome who are alive in the second trimester will not survive to term; thus, the true prevalence of Down's syndrome in the second trimester is closer to 1 in 500 pregnancies. Trisomy 18 (Edwards syndrome) affects 1 in 6,000 births, and trisomy 13 (Patau syndrome) affects 1 in 10,000 births. Sex chromosome aneuploidy (SCA) affects 1 in 400 newborns and is therefore, as a whole, more common than Down's syndrome.

Several counting-based PGS methods exist. A significant fraction of the associated algorithms call copy number based on the fraction of sequencing reads derived from each chromosome (often via comparison to a known non-aneuploid sample). These approaches suffer from the fact that chromosomal read fractions are highly interdependent. For example, the addition or subtraction of one chromosome will cause all other observed read fractions to decrease or increase, respectively, thereby potentially leading to incorrect copy number calls for these chromosomes. While several approaches exist to counteract this issue, such as normalization or rounding, accurately determining chromosome copy numbers remains challenging, especially for highly aneuploid samples.

SUMMARY

The present invention solves the problem of the interdependency of chromosomal read fractions in current analysis processes by scaling the chromosomal read fractions. The present invention improves the accuracy of aneuploidy detection and copy number determination in, for example, embryo-derived samples; circulating fetal cells or nucleic acids; amniocentesis; chorionic villus sampling; circulating and biopsied tumor cells; and pre-implantation genetic screening (PGS) assays.

In one aspect of the invention, the interdependence of chromosomal read fractions is corrected by estimating the DNA content of each experimental sample and utilizing the estimated content to calculate corrected, or scaled, read fractions for each chromosome. Scaling the read fractions for each chromosome allows for accurate identification of copy number determination. The scaling of chromosomal read fractions leads to accurate normalization of experimental data. By first computing scaling factors for each sample, it becomes possible to perform an accurate normalization by estimating the exact number of each chromosome in a given sample. Performing this normalization greatly reduces noise and enhances the ability to call copy number determination accurately.

Accordingly, the invention overcomes the problems found in prior analysis methods. In particular, the invention scales the experimental data to account for the total DNA in a sample. This element of the invention leads to more accurate read fractions which can be further improved via normalization, thereby leading to a significant increase in accuracy of aneuploidy detection.

An aspect of the invention is the varied applicability to the field of embryonic aneuploidy detection and analysis methods. The present invention could be similarly utilized on data from any next generation sequencing (NGS)-based PGS method (e.g. whole-genome amplification followed by shotgun library construction and sequencing), as all methods possess similar biases due to the interdependence of chromosomal read fractions and the lack of accounting for variation in DNA content.

DETAILED DESCRIPTION

Figure 1:
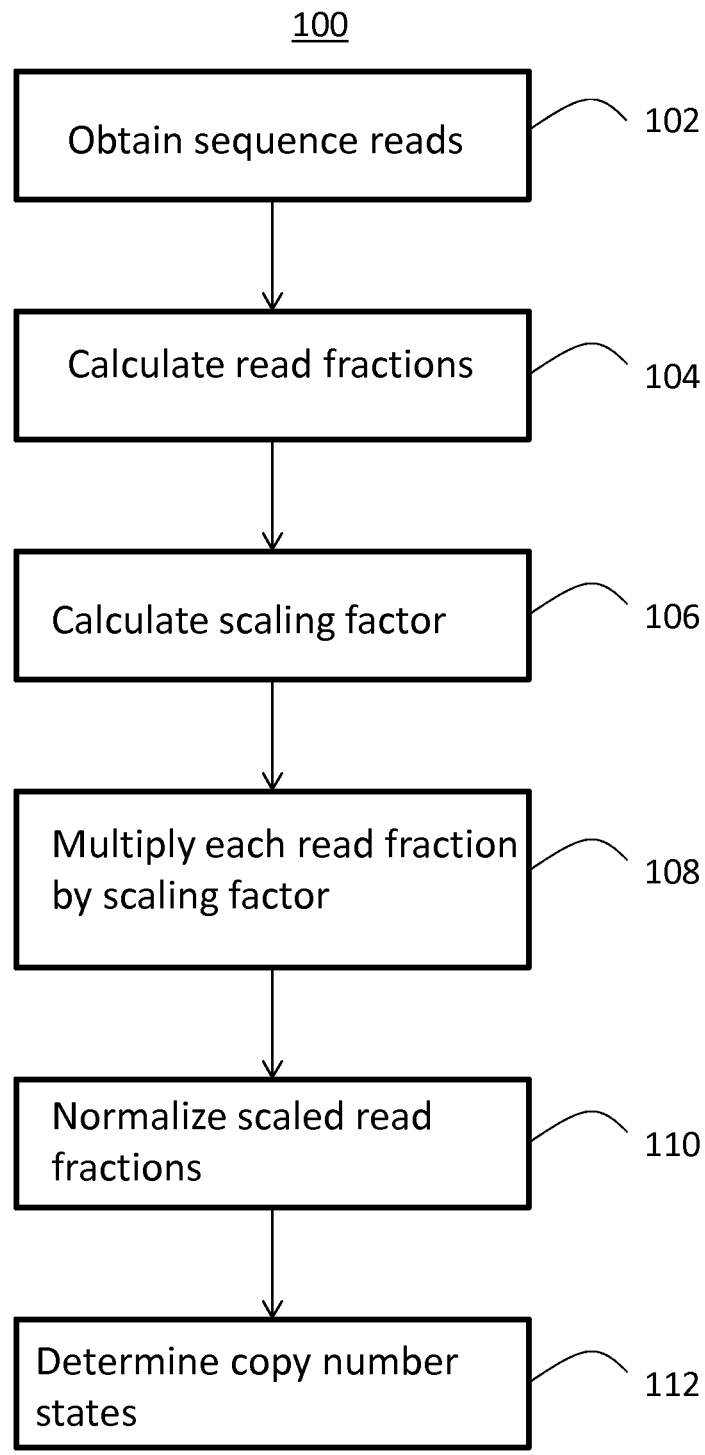
FIG. 1 is a diagram of methods of the invention.

The invention generally relates to methods that improve the accuracy of aneuploidy detection and copy number determination in, for example, embryo-derived samples; circulating fetal cells or nucleic acids; amniocentesis; chorionic villus sampling; circulating and biopsied tumor cells; and pre-implantation genetic screening (PGS) assays. The present invention relates an algorithm in which chromosomal read fractions are scaled to increase the accuracy of normalization and increase the accuracy of detection methods.

Samples and Obtaining Nucleic Acid

In certain aspects, methods of the invention may involve obtaining a sample. The sample is typically a tissue or body fluid that is obtained in any clinically acceptable manner. A tissue is a mass of connected cells and/or extracellular matrix material, e.g. skin tissue, endometrial tissue, trophectoderm biopsy-derived tissue, nasal passage tissue, CNS tissue, neural tissue, eye tissue, liver tissue, kidney tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, menstrual fluid, mammary fluid, follicular fluid of the ovary, fallopian tube fluid, peritoneal fluid, urine, and cerebrospinal fluid (CSF), such as lumbar or ventricular CSF. A sample may also be a fine needle aspirate or biopsied tissue. A sample also may be media containing cells or biological material. A sample may also be a blood clot, for example, a blood clot that has been obtained from whole blood after the serum has been removed. Samples are also obtained from the environment (e.g., air, agricultural, water and soil); and research samples (e.g., samples from cultured or preserved replicative, immortalized, or senescent cell lines, products of a nucleic acid amplification reaction, or purified genomic DNA, RNA, proteins, etc.).

In certain aspects of the invention, the sample may be derived from an embryo or from a fetus, either in utero or prior to transfer or implantation. Genetic material may be obtained prior to fertilization, or the embryo can be fertilized and allowed to develop in vitro for several days until several cells form. For example, at the blastocyst stage of embryo development, a trophectoderm biopsy can be performed. See for example Dokras et al., Trophectoderm biopsy in human blastocysts, Hum. Reprod. (1990) 5 (7): 821-825, the contents of which are incorporated by reference. Genetic material may also be obtained from a polar body biopsy. See for example Montag et al. Polar Body Biopsy, Practical Manual of In Vitro Fertilization, 2012, pp 455-459, the contents of which is incorporated by reference. Genetic material may be obtained directly or indirectly from the embryo or fetus. Furthermore, embryonic nucleic acids can be derived from necrotic or apoptotic embryo material. Furthermore, a sample may be derived from polar body biopsy.

Isolation, extraction or derivation of genomic nucleic acids is performed by methods known in the art. Isolating nucleic acid from a biological sample generally includes treating a biological sample in such a manner that genomic nucleic acids present in the sample are extracted and made available for analysis. Any isolation method that results in extracted/isolated genomic nucleic may be used in the practice of the present invention.

Nucleic acids may be obtained by methods known in the art. Generally, nucleic acids are extracted using techniques, such as those described in Sambrook, J., Fritsch, E. F., and Maniatis, T. (1989) Molecular Cloning: A Laboratory Manual. 2nd ed. Cold Spring Harbor, N.Y.: Cold Spring Harbor Laboratory.), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, Mass.); and Beckman Coulter (Brea, Calif.). For example, Autogen manufactures FlexStar automated extraction kits used in combination with Qiagen FlexiGene Chemistry, and Beckman Coulter manufactures Agencourt GenFind kits for bead-based extraction chemistry. User Guides that describe in detail the protocol(s) to be followed are usually included in all of these kits, for example, Qiagen's literature for their PureGene extraction chemistry entitled "Qiagen PureGene Handbook" 3rd Edition, dated June 2011.

Lysing of the cells can be performed by methods known in the art. After cells have been obtained from the sample, it is preferable to lyse cells in order to isolate genomic nucleic acids. Lysing methods may include sonication, freezing, boiling, exposure to detergents, or exposure to alkali or acidic conditions. The concentration of the detergent can be up to an amount where the detergent remains soluble in the solution. The detergent, particularly one that is mild and nondenaturing, can act to solubilize the sample. Detergents may be ionic or nonionic. Examples of nonionic detergents include triton, such as the Triton® X series (Triton® X-100 t-Oct-C6H4-(OCH2-CH2)xOH, x=9-10, Triton® X-100R, Triton® X-114 x=7-8), octyl glucoside, polyoxyethylene(9) dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl) dimethyl-ammonio]-1-propanesulfonate. It is contemplated also that urea may be added with or without another detergent or surfactant.

Lysis or homogenization solutions may further contain other agents, such as reducing agents. Examples of such reducing agents include dithiothretol (DTT), β-mercaptoethanol, DTE, GSH, cysteine, cysteamine, tricarboxyethyl phosphine (TCEP), or salts of sulfurous acid.

Cellular extracts can be subjected to other steps to drive nucleic acid isolation toward completion by, e.g., differential precipitation, column chromatography, electrophoresis, extraction with organic solvents and the like. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. The genomic nucleic acid can also be resuspended in a hydrating solution, such as an aqueous buffer. The genomic nucleic acid can be suspended in, for example, water, Tris buffers, or other buffers. In certain embodiments the genomic nucleic acid can be resuspended in Qiagen DNA hydration solution, or other Tris-based buffer of a pH of around 7.5.

Depending on the type of method used for extraction, the genomic nucleic acid obtained can vary in size. The integrity and size of genomic nucleic acid can be determined by pulse-field gel electrophoresis (PFGE) using an agarose gel.

In addition to genomic nucleic acids, whole genome amplification product and partial genomic amplification products can be used in aspects of the invention. Methods of obtaining whole genome amplification product and partial genome amplification product are described in detail in Pinter et al. U.S. Patent Publication Number 2004/0209299, and include, for example, generally ligation mediated PCR, random primed PCR, strand displacement mediated PCR, and cell immortalization.

In certain embodiments, a genomic sample is collected from a subject followed by enrichment for genes or gene fragments of interest, for example by hybridization to a nucleotide array. The sample may be enriched for genes of interest using methods known in the art, such as hybrid capture. See for examples, Lapidus (U.S. Pat. No. 7,666,593), the content of which is incorporated by reference herein in its entirety. As will be described in more detail below, a preferable capture method uses molecular inversion probes or other polymerase chain reaction based methodologies.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. The genomic nucleic acid fragments can range from 1 kilobase to 20 kilobases. Fragments can vary in size and have an average fragment length of about 10 kilobases. The particular method of fragmenting is selected to achieve the desired fragment length.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

In one aspect, a nucleic acid is fragmented by heating a nucleic acid immersed in a buffer system at a certain temperature for a certain period of time to initiate hydrolysis and thus fragment the nucleic acid. The pH of the buffer system, duration of heating, and temperature can be varied to achieve a desired fragmentation of the nucleic acid. In one embodiment, after a genomic nucleic acid is purified, it is resuspended in a Tris-based buffer at a pH between 7.5 and 8.0, such as Qiagen's DNA hydrating solution. The resuspended genomic nucleic acid is then heated to 65° C. and incubated overnight (about 16-24 hours) at 65° C. Heating shifts the pH of the buffer into the low- to mid-6 range, which leads to acid hydrolysis. Over time, the acid hydrolysis causes the genomic nucleic acid to fragment into single-stranded and/or double-stranded products.

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids or strong bases.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH ([OH—] concentration to 0.1 N) is added, and the sample is stirred until the DNA redissolves completely. The sample is then incubated at 65° C. for 30 minutes in order to hydrolyze the DNA. Resulting fragments typically range from about 250-1000 nucleotides but can vary lower or higher depending on the conditions of hydrolysis.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oelher et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonification is described in U.S. Patent Publication 2009/0233814. In the method, a purified nucleic acid is obtained and placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948, 843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with BIORUPTOR (ultrasonicator device, commercially available from Diagenode, Inc.). Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing of nucleic acid into fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Krüger D H (June 1993). "Biology of DNA restriction". Microbiol. Rev. 57 (2): 434-50; Boyer H W (1971). "DNA restriction and modification mechanisms in bacteria". Annu Rev. Microbiol. 25: 153-76; Yuan R (1981). "Structure and mechanism of multifunctional restriction endonucleases". Annu Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequences in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

In some embodiments of the invention, a library construction method that combines simultaneous fragmentation of DNA and ligation of adapter sequences in a single reaction mediated by a transposase loaded with adapter oligos may be utilized. See for example, Adey et al., Rapid, low-input, low-bias construction of shotgun fragment libraries by high-density in vitro transposition, Genome Biol. 2010, 11:R119, the contents of which is incorporated by reference. This technique, referred to as tagmentation, can produce high-quality genomic or cDNA libraries from as little as 20 pg DNA, reducing both preparation time and input material. See for example, Parkinson et al., Preparation of high-quality next-generation sequencing libraries from picogram quantities of target DNA, Genome Res 2012, 22:125-133, the contents of which is incorporated by reference.

Denaturing the Nucleic Acids

Methods of the invention also provide for denaturing nucleic acid to render the nucleic acid single stranded for hybridization to a capture probe, such as a MIP probe. Denaturation can result from the fragmentation method chosen, as described above. For example, one skilled in the art recognizes that a genomic nucleic acid can be denatured during pH-based shearing or fragmenting via nicking endonucleases. Denaturation can occur either before, during, or after fragmentation. In addition, the use of pH or heat during the fragmenting step can result in denatured nucleic acid fragments. See, for example, McDonnell, "Antisepsis, disinfection, and sterilization: types, action, and resistance," pg. 239 (2007).

Heat-based denaturing is the process by which double-stranded deoxyribonucleic acid unwinds and separates into single-stranded strands through the breaking of hydrogen bonding between the bases. Heat denaturation of a nucleic acid of an unknown sequence typically uses a temperature high enough to ensure denaturation of even nucleic acids having a very high GC content, e.g., 95° C.-98° C. in the absence of any chemical denaturant. It is well within the abilities of one of ordinary skill in the art to optimize the conditions (e.g., time, temperature, etc.) for denaturation of the nucleic acid. Temperatures significantly lower than 95° C. can also be used if the DNA contains nicks (and therefore sticky overhangs of low Tm) or sequence of sufficiently low Tm.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Dore et al. Biophys J. 1969 November; 9(11): 1281-1311; A. M. Michelson The Chemistry of Nucleosides and Nucleotides, Academic Press, London and New York (1963).

Nucleic acids can also be denatured via electro-chemical means, for example, by applying a voltage to a nucleic acid within a solution by means of an electrode. Varying methods of denaturing by applying a voltage are discussed in detail in U.S. Pat. Nos. 6,197,508 and 5,993,611.

Amplification and PCR Based Detection Methods

With polymerase chain reaction (PCR), it is possible to amplify a single copy of a specific target sequence in genomic DNA to a level that can be detected by several different methodologies (e.g., staining, hybridization with a labeled probe, incorporation of biotinylated primers followed by avidin-enzyme conjugate detection, incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification-based methods include amplification of a single target nucleic acid and multiplex amplification (amplification of multiple target nucleic acids in parallel). In various embodiments, the nucleic acid is amplified, for example, from the sample or after isolation from the sample. Amplification refers to production of additional copies of a nucleic acid sequence and is generally conducted using polymerase chain reaction (PCR) or other technologies well-known in the art (e.g., Dieffenbach and Dveksler, PCR Primer, a Laboratory Manual, 1995, Cold Spring Harbor Press, Plainview, N.Y.). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany, F. Genome research, 1:5-16 (1991); Barany, F., PNAS, 88:189-193 (1991); U.S. Pat. Nos. 5,869,252; and 6,100,099), strand displacement amplification and restriction fragment length polymorphism, transcription based amplification system, rolling circle amplification, and hyper-branched rolling circle amplification. Further examples of amplification techniques that can be used include, without limitation, quantitative PCR, quantitative fluorescent PCR (QF-PCR), multiplex fluorescent PCR (MF-PCR), real time PCR (RTPCR), single cell PCR, restriction fragment length polymorphism (PCR-RFLP), RT-PCR-RFLP, hot start PCR, in situ polonony PCR, in situ rolling circle amplification (RCA), bridge PCR, picotiter PCR, and emulsion PCR. Other suitable amplification methods include transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In certain embodiments, the amplification reaction is the polymerase chain reaction. Polymerase chain reaction refers to methods by K. B. Mullis (U.S. Pat. Nos. 4,683,195 and 4,683,202, hereby incorporated by reference) for increasing concentration of a segment of a target sequence in a mixture of genomic DNA without cloning or purification.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software from Arrayit Corporation (Sunnyvale, Calif.), Oligonucleotide Probe Sequence Design Software for Genetic Analysis from Olympus Optical Co., Ltd. (Tokyo, Japan), NetPrimer, and DNAsis Max v3.0 from Hitachi Solutions America, Ltd. (South San Francisco, Calif.). The TM (melting or annealing temperature) of each primer is calculated using software programs such as OligoAnalyzer 3.1, available on the web site of Integrated DNA Technologies, Inc. (Coralville, Iowa).

Amplification adapters may be attached to the fragmented nucleic acid. Adapters may be commercially obtained, such as from Integrated DNA Technologies (Coralville, Iowa). In certain embodiments, the adapter sequences are attached to the template nucleic acid molecule with an enzyme. The enzyme may be a ligase or a polymerase. The ligase may be any enzyme capable of ligating an oligonucleotide (RNA or DNA) to the template nucleic acid molecule. Suitable ligases include T4 DNA ligase and T4 RNA ligase, available commercially from New England Biolabs (Ipswich, Mass.).

Methods for using ligases are well known in the art. The polymerase may be any enzyme capable of adding nucleotides to the 3' and the 5' terminus of template nucleic acid molecules.

In one embodiment of the invention, the target nucleic acid and nucleic acid ligand can be detected using detectably labeled probes. Nucleic acid probe design and methods of synthesizing oligonucleotide probes are known in the art. See, e.g., Sambrook et al., DNA microarray: A Molecular Cloning Manual, Cold Spring Harbor, N.Y., (2003) or Maniatis, et al., Molecular Cloning: A Laboratory Manual, Cold Spring Harbor, N.Y., (1982), the contents of each of which are herein incorporated by reference herein in their entirety. Sambrook et al., Molecular Cloning: A Laboratory Manual (2nd Ed.), Vols. 1-3, Cold Spring Harbor Laboratory, (1989) or F. Ausubel et al., Current Protocols In Molecular Biology, Greene Publishing and Wiley-Interscience, New York (1987), the contents of each of which are herein incorporated by reference in their entirety. Suitable methods for synthesizing oligonucleotide probes are also described in Caruthers, Science, 230:281-285, (1985), the contents of which are incorporated by reference.

Probes suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Probes can be single stranded or double stranded. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA.

The length of the nucleotide probe is not critical, as long as the probes are capable of hybridizing to the target nucleic acid and nucleic acid ligand. In fact, probes may be of any length. For example, probes may be as few as 5 nucleotides, or as much as 5000 nucleotides. Exemplary probes are 5-mers, 10-mers, 15-mers, 20-mers, 25-mers, 50-mers, 100-mers, 200-mers, 500-mers, 1000-mers, 3000-mers, or 5000-mers. Methods for determining an optimal probe length are known in the art. See, e.g., Shuber, U.S. Pat. No. 5,888,778, hereby incorporated by reference in its entirety.

Probes used for detection may include a detectable label, such as a radiolabel, fluorescent label, or enzymatic label. See for example Lancaster et al., U.S. Pat. No. 5,869,717, hereby incorporated by reference. In certain embodiments, the probe is fluorescently labeled. Fluorescently labeled nucleotides may be produced by various techniques, such as those described in Kambara et al., Bio/Technol., 6:816-21, (1988); Smith et al., Nucl. Acid Res., 13:2399-2412, (1985); and Smith et al., Nature, 321: 674-679, (1986), the contents of each of which are herein incorporated by reference in their entirety. The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, (1991); Zuckerman et al., Polynucleotides Res., 15: 5305-5321, (1987); Sharma et al., Polynucleotides Res., 19:3019, (1991); Giusti et al., PCR Methods and Applications, 2:223-227, (1993); Fung et al. (U.S. Pat. No. 4,757,141); Stabinsky (U.S. Pat. No. 4,739,044); Agrawal et al., Tetrahedron Letters, 31:1543-1546, (1990); Sproat et al., Polynucleotides Res., 15:4837, (1987); and Nelson et al., Polynucleotides Res., 17:7187-7194, (1989), the contents of each of which are herein incorporated by reference in their entirety. Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra The detectable label attached to the probe may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N[3-vinylsulfonyl)phenyl]naphthalimide-3,5 disulfonate; N-(4-anilino-1-naphthyl)maleimide; anthranilamide; BODIPY; alexa; fluorescien; conjugated multi-dyes; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

Detection of a bound probe may be measured using any of a variety of techniques dependent upon the label used, such as those known to one of skill in the art. Exemplary detection methods include radioactive detection, optical absorbance detection, e.g., UV-visible absorbance detection, optical emission detection, e.g., fluorescence or chemiluminescence. Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993)), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc.

In certain embodiments, nucleic acid targets can also be identified, or confirmed using a microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Methods for making microarrays and determining gene product expression (e.g., RNA or protein) are shown in Yeatman et al. (U.S. patent application number 2006/0195269), the content of which is incorporated by reference herein in its entirety. PCR products are applied to a substrate in a dense array, for example, at least 10,000 nucleotide sequences are applied to the substrate. The microarrayed genes, immobilized on the microchip at 10,000 elements each, are suitable for hybridization under stringent conditions. Labeled probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding nucleic acid target abundance. Microarray analysis can be performed by commercially available equipment, following manufacturer's protocols, such as by using the Affymetrix GenChip technology, or Incyte's microarray technology.

In certain embodiments, the target nucleic acid or nucleic acid ligand or both are quantified using methods known in the art. A preferred method for quantitation is quantitative polymerase chain reaction (QPCR). As used herein, "QPCR" refers to a PCR reaction performed in such a way and under such controlled conditions that the results of the assay are quantitative, that is, the assay is capable of quantifying the amount or concentration of a nucleic acid ligand present in the test sample.

QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of PCR, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), (2006)), Heid et al. (Genome Research 986-994, (1996)), Sambrook and Russell (Quantitative PCR, Cold Spring Harbor Protocols, (2006)), and Higuchi (U.S. Pat. Nos. 6,171,785 and 5,994,056). The contents of these are incorporated by reference herein in their entirety.

Two common methods of quantification are: (1) use of fluorescent dyes that intercalate with double-stranded DNA, and (2) modified DNA oligonucleotide probes that fluoresce when hybridized with a complementary DNA.

In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification, it is important to normalize expression of a target gene to a stably expressed gene. This allows for correction of possible differences in nucleic acid quantity or quality across samples.

The second method uses sequence-specific RNA or DNA-based probes to quantify only the DNA containing the probe sequence; therefore, use of the reporter probe significantly increases specificity, and allows for quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR, both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

In certain embodiments, the QPCR reaction uses fluorescent Taqman™ methodology and an instrument capable of measuring fluorescence in real time (e.g., ABI Prism 7700 Sequence Detector; see also PE Biosystems, Foster City, Calif.; see also Gelfand et al., (U.S. Pat. No. 5,210,015), the contents of which is hereby incorporated by reference in its entirety). The Taqman™ reaction uses a hybridization probe labeled with two different fluorescent dyes. One dye is a reporter dye (6-carboxyfluorescein), the other is a quenching dye (6-carboxy-tetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra.

The nucleic acid ligand of the present invention is quantified by performing QPCR and determining, either directly or indirectly, the amount or concentration of nucleic acid ligand that had bound to its probe in the test sample. The amount or concentration of the bound probe in the test sample is generally directly proportional to the amount or concentration of the nucleic acid ligand quantified by using QPCR. See for example Schneider et al., U.S. Patent Application Publication Number 2009/0042206, Dodge et al., U.S. Pat. No. 6,927,024, Gold et al., U.S. Pat. Nos. 6,569,620, 6,716,580, and 7,629,151, Cheronis et al., U.S. Pat. No. 7,074,586, and Ahn et al., U.S. Pat. No. 7,642,056, the contents of each of which are herein incorporated by reference in their entirety.

Digital PCR (dPCR) is an alternative quantitation method known in the art, in which dilute samples are divided into many separate reactions. See for example, United States Patent Application 20130178378, which is incorporated by reference. With digital PCR (dPCR), a sample is partitioned so that individual nucleic acid molecules within the sample are localized and concentrated within many separate regions. The partitioning of the sample allows the molecules to be counted by estimating according to a Poisson distribution. As a result, each part will contain "0" or "1" molecules, or a negative or positive reaction, respectively. After PCR amplification, nucleic acids may be quantified by counting the regions that contain PCR end-product, positive reactions. In conventional PCR, the starting copy number is proportionally quantified to the number of PCR amplification cycles required to reach a threshold fluorescence intensity. Digital PCR, however, is not dependent on the number of amplification cycles to determine the initial sample amount, eliminating the reliance on uncertain exponential data to quantify target nucleic acids and providing absolute quantification.

Multiplex polymerase chain reaction (Multiplex PCR) is another modification of polymerase chain reaction and is used in order to rapidly detect multiple gene sequences in a single PCR reaction. Multiplex PCR is typically accomplished using multiple primer sequences, each with a unique fluorophore for detection and quantification. This process amplifies DNA samples using the primers along with temperature-mediated DNA polymerases in a thermal cycler. Multiplex-PCR consists of multiple primer sets within a single PCR mixture to produce amplicons that are specific to different DNA sequences.

Typically, as much as 5-plex real-time qPCR is achievable in a PCR mixture by using fluorescently labeled probes, each one corresponding to a unique DNA sequence, which when amplified by a DNA polymerase, emit a fluorescence signal at its specified spectral wavelength. The spectral frequency discrimination between different fluorophores, or reporters, attached to each probe sequence enables detection of up to five different amplicon sequences, one for each fluorescent color that can be identified. Multiplexing beyond 5-plex is difficult due to insufficient spectral wavelengths that can be optically distinguished using current state of the art fluorescence excitation and emission filter sets.

Multiplex amplification strategies may be used analytically, as in detection methodologies, or preparatively, often for next-generation sequencing or other sequencing techniques. In the preparative setting, the output of an amplification reaction is generally the input to a shotgun library protocol, which then becomes the input to the sequencing platform. The shotgun library is necessary in part because next-generation sequencing yields reads significantly shorter than amplicons such as exons.

Other amplification technologies may be used with the present invention. For example, common amplification methods such as PCR rely on primer binding sites on either side of a target sequence. A set of multiple overlapping amplicons can be targeted to cover a long segment of DNA. While so far amplicon-based sequencing methods have been used to take a targeted look at specific mutations, there is increasing interest in using these methods on a larger scale to sequence longer segments of the genome or exome. Based on ultrahigh-multiplex PCR, Ion AmpliSeq™ technology requires 10 ng of input DNA to target sets of genes, allowing for sequencing of formalin-fixed, paraffin-embedded (FFPE) samples. Alternative target selection methods are lengthy and complex and require large amounts of DNA. Using FFPE DNA and one pool of 6,144 primer pairs, variants can be identified using the Ion AmpliSeq™ Custom workflow. See for example, Ion Torrent's technique to sequence whole exomes by targeting 300,000 different amplicons, 'Rapid exome sequencing using the ion proton system and ion ampliseq technology', a 2013 Application Note from Life Technologies Corporation, Carlsbad, Calif. (5 pages), the contents of which are incorporated by reference.

Molecular inversion probe technology can also be used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

Molecular inversion probes include a universal portion flanked by two unique targeting arms. The targeting arms are designed to hybridize immediately upstream and downstream of a specific target sequence located on a genomic nucleic acid fragment. The molecular inversion probes are introduced to nucleic acid fragments to perform capture of target sequences located on the fragments. According to the invention, fragmenting aids in capture of target nucleic acid by molecular inversion probes. As described in greater detail herein, after capture of the target sequence (e.g., locus) of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat Methods. 2009 Apr. 6:1-2.).

In some methods, a library of molecular inversion probes is generated, wherein the probes are used in capturing DNA of genomic regions of interests (e.g., repetitive elements). The library consists of a plurality of oligonucleotide probes capable of capturing one or more genomic regions of interest (e.g., repetitive elements) within the samples to be tested.

The result of MIP capture as described above is a library of circular target probes, which then can be processed in a variety of ways. In one aspect, adaptors for sequencing can be attached during common linker-mediated PCR, resulting in a library with non-random, fixed starting points for sequencing. In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

It should be appreciated that methods can vary the amounts of genomic nucleic acid and vary the amounts of MIP probes to reach a customized result. In some methods, the amount of genomic nucleic acid used per subject ranges from 1 ng to 10 µg (e.g., 500 ng to 5 µg). However, higher or lower amounts (e.g., less than 1 ng, more than 10 µg, 10-50 µg, 50-100 µg or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some methods, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some methods, probes or regions of probes or other nucleic acids are described herein as including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, etc.).

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 by (as used herein, a by refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is also to be appreciated that some target nucleic acids on a nucleic acid fragment are too large to be captured with one probe. Consequently, it may be necessary to capture multiple subregions of a target nucleic acid in order to analyze the full target.

In some methods, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 by or more. In other methods, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 by or more) longer than corresponding target (e.g., subregion of a target nucleic acid, target nucleic acid). In some methods, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid. Other MIP capture techniques are shown in co-owned and pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Molecular Barcoding

As stated above, polymerase chain reaction methods can be used to detect or amplify particular nucleic acid sequences in complex mixtures. With these methods, a single copy of a specific target nucleic acid may be amplified using a pair of oligonucleotide primers to a level that can be sequenced. Single primer sets may also be utilized to amplify multiple target regions, as previously demonstrated (Kinde et al. 2012 PLoS ONE 7:e41162). Further, the amplified segments created by an amplification process such as PCR may be efficient templates for subsequent PCR amplifications.

Amplification or sequencing adapters or barcodes, or a combination thereof, may be attached to a fragmented nucleic acid molecule. Such molecules may be commercially obtained, such as from Integrated DNA Technologies (Coralville, Iowa). In certain embodiments, such sequences are attached to the template nucleic acid molecule with an enzyme such as a polymerase or ligase. Suitable ligases include T4 DNA ligase and T4 RNA ligase, available commercially from New England Biolabs (Ipswich, Mass.). The ligation may be blunt ended or via use of complementary overhanging ends. In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, Wis.). Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain applications, one or more barcode is attached to each, any, or all of the fragments. A barcode sequence generally includes certain features that make the sequence useful in sequencing reactions. The barcode sequences are designed such that each sequence is correlated to a particular portion of nucleic acid, allowing sequence reads to be correlated back to the portion from which they came. Methods of designing sets of barcode sequences are shown for example in U.S. Pat. No. 6,235,475, the content of which is incorporated by reference herein in its entirety. In certain embodiments, the bar code sequences range from about 5 nucleotides to about 15 nucleotides. In a particular embodiment, the barcode sequences range from about 4 nucleotides to about 7 nucleotides. In certain embodiments, the barcode sequences are attached to the template nucleic acid molecule, e.g., with an enzyme. The enzyme may be a ligase or a polymerase, as discussed above. Attaching barcode sequences to nucleic acid templates is shown in U.S. Pub. 2008/0081330 and U.S. Pub. 2011/0301042, the content of each of which is incorporated by reference herein in its entirety. Methods for designing sets of barcode sequences and other methods for attaching barcode sequences are shown in U.S. Pat. Nos. 6,138,077; 6,352,828; 5,636,400;

6,172,214; 6235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. After any processing steps (e.g., obtaining, isolating, fragmenting, amplification, or barcoding), nucleic acid can be sequenced.

Sequencing

Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

In some embodiments, a sequencing technique (e.g., a next-generation sequencing technique) is used to sequence part of one or more captured targets (e.g., or amplicons thereof) and the sequences are used to count the number of different barcodes that are present. Accordingly, in some embodiments, aspects of the invention relate to a highly-multiplexed qPCR reaction.

A sequencing technique that can be used includes, for example, Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which is incorporated by reference in their entirety.

Sequencing generates a plurality of reads. Reads generally include sequences of nucleotide data less than about 150 bases in length, or less than about 90 bases in length. In certain embodiments, reads are between about 80 and about 90 bases, e.g., about 85 bases in length. In some embodiments, these are very short reads, i.e., less than about 50 or about 30 bases in length.

A sequencing technique that can be used in the methods of the provided invention includes, for example, 454 sequencing (454 Life Sciences, a Roche company, Branford, Conn.) (Margulies, M et al., Nature, 437:376-380 (2005); U.S. Pat. Nos. 5,583,024; 5,674,713; and 5,700,673). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing, described, for example, in U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton (H.sup.+), which signal is detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each of which are herein incorporated by reference in their entirety.

Another example of a sequencing technology that can be used in the methods of the provided invention includes the single molecule, real-time (SMRT) technology of Pacific Biosciences (Menlo Park, Calif.). In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni, G. V., and Meller, A., Clin Chem 53: 1996-2001 (2007)). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in U.S. Pub. 2009/0026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using an electron microscope (Moudrianakis E. N. and Beer M., PNAS, 53:564-71(1965)). In one example of the technique, individual DNA molecules are labeled using metallic labels that are distinguishable using an electron microscope. These molecules are then stretched on a flat surface and imaged using an electron microscope to measure sequences.

Another example of a sequencing technique that can be used in the methods of the provided invention involves Fast Aneuploidy Screening Test-Sequencing System (FAST-SeqS), as described in PCT application PCT/US2013/033451, the contents of which is incorporated by reference. See also Kinde et al., "FAST-SeqS: A Simple and Efficient Method for the Detection of Aneuploidy by Massively Parallel Sequencing," DOI: 10.1371/journal.pone.0041162, the contents of which is incorporated by reference. FAST-SeqS uses specific primers, specifically, a single pair of primers that anneal to a subset of sequences dispersed throughout the genome. The regions are selected due to similarity so that they could be amplified with a single pair of primers, but sufficiently unique to allow most of the amplified loci to be distinguished. FAST-SeqS simplifies prior processes by defining a number of fragments from throughout the genome and amplifying using a single primer pair, obviating the need for end-repair, terminal 3'dA addition, or ligation to adapters. The smaller number of fragments to be assessed, compared to the whole genome, streamlines the genome matching and analysis processes. FAST-SeqS yielded sequences align to a smaller number of positions, as opposed to traditional whole genome amplification libraries in which each tag must be independently aligned.

There are currently many genomic assays that utilize next-generation (e.g., polony-based) sequencing to generate data, including genome resequencing, RNA-seq for gene expression, bisulphite sequencing for methylation, and Immune-seq, among others. In order to make quantitative measurements, these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. Current assays use one of several alternative nucleic acid preparative techniques (e.g., amplification, for example PCR-based amplification; sequence-specific capture, for example, using immobilized capture probes; or target capture into a circularized probe followed by a sequence analysis step. In order to reduce errors associated with the unpredictability (stochastic nature) of nucleic acid isolation and sequence analysis techniques, current methods to involve oversampling a target nucleic acid preparation in order to increase the likelihood that all sequences that are present in the original nucleic acid sample will be represented in the final sequence data. For example, a genomic sequencing library may contain an over- or under-representation of particular sequences from a source nucleic acid sample (e.g., genome preparation) as a result of stochastic variations in the library construction process.

The sequence reads, obtained from any sequencing method, are analyzed. Analysis can include any method known in the art, such as de novo assembly, alignment to a reference, or a combination thereof. In some embodiments, the sequence reads are assembled into a contig. The contig can be aligned to a reference genome. In certain embodiments, individual reads are then aligned back to the contig.

Sequence assembly can be done by methods known in the art including reference-based assemblies, de novo assemblies, assembly by alignment, or combination methods. Assembly can include methods described in U.S. Pat. No. 8,209,130 titled Sequence Assembly by Porecca and Kennedy, the contents of each of which are hereby incorporated by reference in their entirety for all purposes. In some embodiments, sequence assembly uses the low coverage sequence assembly software (LOCAS) tool described by Klein, et al., in LOCAS-A low coverage sequence assembly tool for re-sequencing projects, PLoS One 6(8) article 23455 (2011), the contents of which are hereby incorporated by reference in their entirety. Sequence assembly is described in U.S. Pat. Nos. 8,165,821; 7,809,509; 6,223,128; U.S. Pub. 2011/0257889; and U.S. Pub. 2009/0318310, the contents of each of which are hereby incorporated by reference in their entirety.

Data Analysis

Read counts are analyzed to determine copy number states of genomic regions of interest. Read counts can be obtained from any of the methods discussed above, including but not limited to, PCR based methodologies, such as digital PCR or multiplexing PCR; microarray; or sequencing. A set of read counts can be analyzed by any suitable method known in the art. For example, in some embodiments, read counts are analyzed by hardware or software provided as part of a sequence instrument. In some embodiments, individual read counts are reviewed by sight (e.g., on a computer monitor). A computer program may be written that pulls an observed genotype from individual reads.

FIG. 1 is a flow diagram illustrating one embodiment of a method for determining copy number state of one of more genomic regions of interest in a sample. The method 100 includes obtaining sequence reads (operation 102) and calculating the read fraction (operation 104). As described in greater detail herein, read counts for a genomic region of interest are normalized with respect to an internal control DNA. The method 100 further includes calculating a sample specific scaling factor (operation 106), and multiplying this scaling factor by each read fraction (operation 108). The scaled chromosomal read fractions are normalized (operation 110). The method further includes determining a copy number state of the chromosomes (operation 112) based on the comparison, specifically the ratio.

To enable accurate copy number determination, the algorithm of the present invention corrects for the error(s) introduced by the interdependence (members of the group are mutually dependent on the others) of chromosomal read fractions. The algorithm involves estimating the DNA content of each experimental sample and utilizing this estimated content to calculate corrected, or scaled, read fractions for each chromosome. As part of the analysis and determination of copy number states and subsequent identification of copy number variation, the fraction of total reads mapping to a chromosome, called the chromosomal read fraction, is calculated according to the following formula:

$$r_n = \frac{m_n}{\sum_{n=1,2,3...}^{Y} (m_n)}$$

where m represents the number of mapped reads on a given chromosome n (1, 2, 3 . . . Y). The chromosomal read fraction is computed assuming euploid DNA content. To account for the difference in total DNA content between the experimental sample and a euploid control sample (or set of samples), a sample-specific scaling factor is determined and then each chromosomal read fraction is multiplied by the scaling factor, S.

In order to determine the total DNA content of each sample, a scaling factor is chosen such that the total distance between the observed read fraction and the nearest whole number multiple of a euploid read fraction (generally determined empirically from euploid samples) for each chromosome is minimized. In other words, a scaling factor S is chosen such that for a given set of read fractions $r_n$ the following value, D, is minimized:

$$D = \sum_{n=1,2,3...}^{Y} \text{abs}\left(1 - \frac{2S \frac{r_{n,experimental}}{r_{n,euploid}}}{\text{round}\left(2S \frac{r_{n,experimental}}{r_{n,euploid}}\right)}\right)$$

After this optimization, the scaling factor S represents the difference in DNA content between the experimental sample and a euploid sample; for example, if S is equal to 1.04, the experimental sample possesses 4% more DNA than a euploid sample. After determining each sample's DNA content in this manner, each chromosomal read fraction is multiplied by the scaling factor, so the values can be compared between aneuploid and euploid samples without any under or overestimation due to read fraction interdependence. The calculation of the cellular DNA content is based upon the assumption that most, if not all, samples should carry whole number copies of each chromosome. Thus, if a sample's chromosomal read fractions are computed using the correct total DNA content, each observed read fraction should be a whole number multiple of the read fraction observed for the corresponding chromosome in euploid samples.

The scaling of chromosomal read fractions allow for accurate normalization of experimental data. While in many types of genomic analyses normalization procedures are performed to reduce stochastic variability due to experimental and sampling variation, in the case of PGS, the assumptions inherent in most normalization methods do not apply due to the potentially wide variety of the number of chromosomes in each sample; thus, performing normalization in such cases may result in true aneuploidy being missed (e.g. a false negative). Increased accuracy in the normalization step also reduces the changes of reporting a false positive. However, by first computing scaling factors for each sample as described above, it becomes possible to perform an accurate normalization by estimating the exact number of each chromosome in a given sample. While the chromosomal read fraction will vary across samples due to aneuploidy, the quantity:

$$i_{n,experimental} = \frac{r_{n,experimental}}{\text{round}\left(2S\frac{r_{n,experimental}}{r_{n,euploid}}\right)}$$

or the read fraction per individual chromosome, should be invariant (unaltered, unchanged) across all samples. This quantity can be computed for each chromosome in each sample, and quantile or other normalization approaches can then be performed to equate the distribution of read fractions per individual chromosome across all samples. Performing this normalization greatly reduces noise and enhances the ability to call copy number variation accurately; this is only possible due to knowing the total DNA content of each sample.

Functions described above can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system 200 for implementing some or all of the described inventive methods can include one or more processors (e.g., a central processing unit (CPU) a graphics processing unit (GPU), or both), main memory and static memory, which communicate with each other via a bus.

Figure 2:
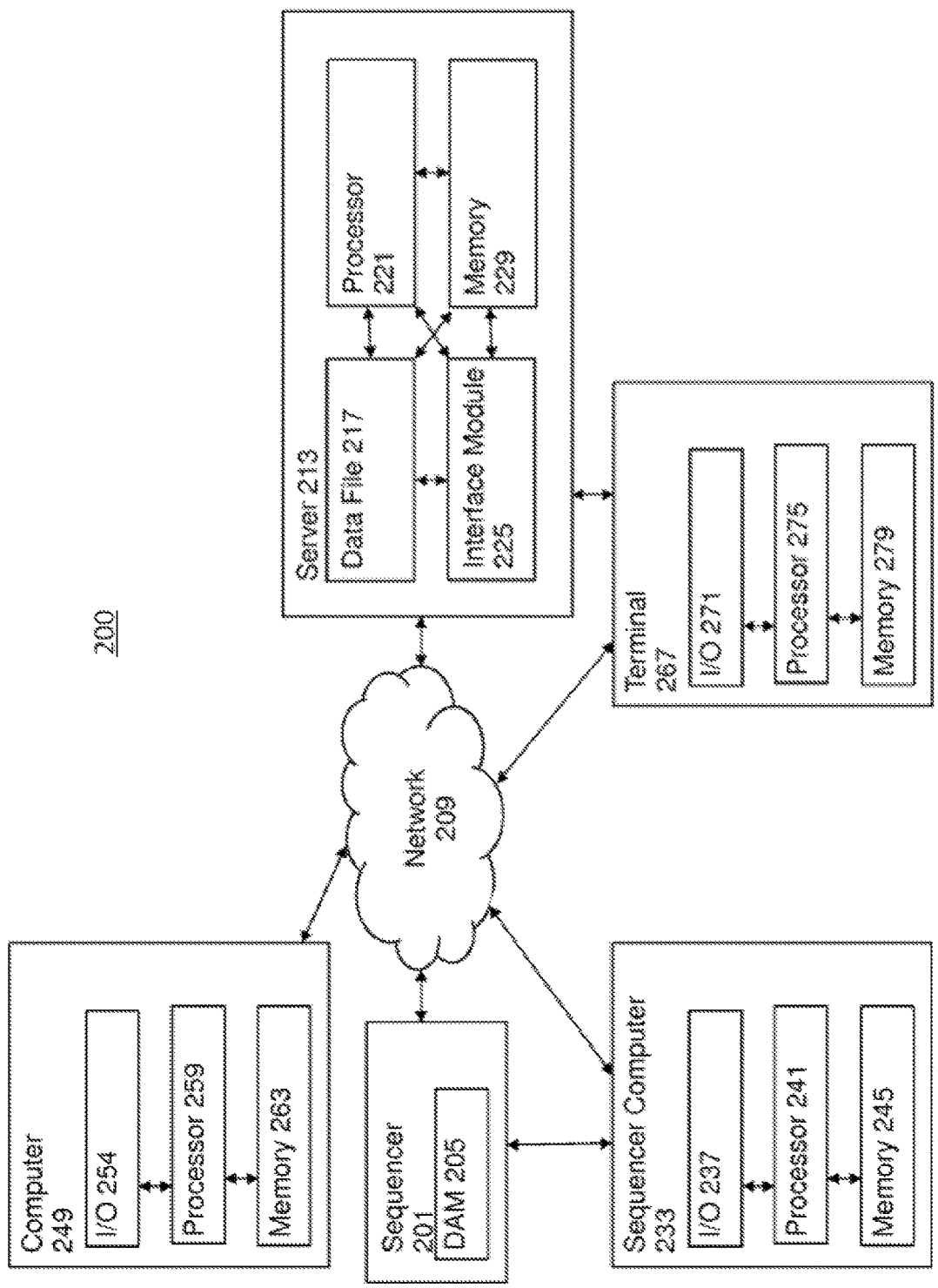
FIG. 2 illustrates a system for performing methods of the invention.

In an exemplary embodiment shown in FIG. 2, system 200 includes a sequencer 201 with a data acquisition module 205 to obtain sequence read data. The sequencer 201 may optionally include or be operably coupled to its own, e.g., dedicated, sequencer computer 233 (including an input/output mechanism 237, one or more of processor 241, and memory 245). Additionally or alternatively, the sequencer 201 may be operably coupled to a server 213 or computer 249 (e.g., laptop, desktop, or tablet) via a network 209. As previously described herein, the sequencer 201 may include the HiSeq 2500/1500 system sold by Illumina, Inc. (San Diego, Calif.).

The computer 249 includes one or more processors 259 and memory 263 as well as an input/output mechanism 254. Where methods of the invention employ a client/server architecture, steps of methods of the invention may be performed using the server 213, which includes one or more of processors 221 and memory 229, capable of obtaining data, instructions, etc., or providing results via an interface module 225 or providing results as a file 217. The server 213 may be engaged over the network 209 by the computer 249 or the terminal 267, or the server 213 may be directly connected to the terminal 267, which can include one or more processors 275 and memory 279, as well as an input/output mechanism 271.

The system or machines 200 according to the invention may further include, for any of I/O 249, 237, or 271, a video display unit (e.g., a liquid crystal display (LCD) or a cathode ray tube (CRT)). Computer systems or machines used to implement some or all of the invention can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 263, 245, 279, or 229 can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro SD card, or solid-state drive (SSD)), optical and magnetic media, and/or any other tangible storage medium or media.

Figure 3:
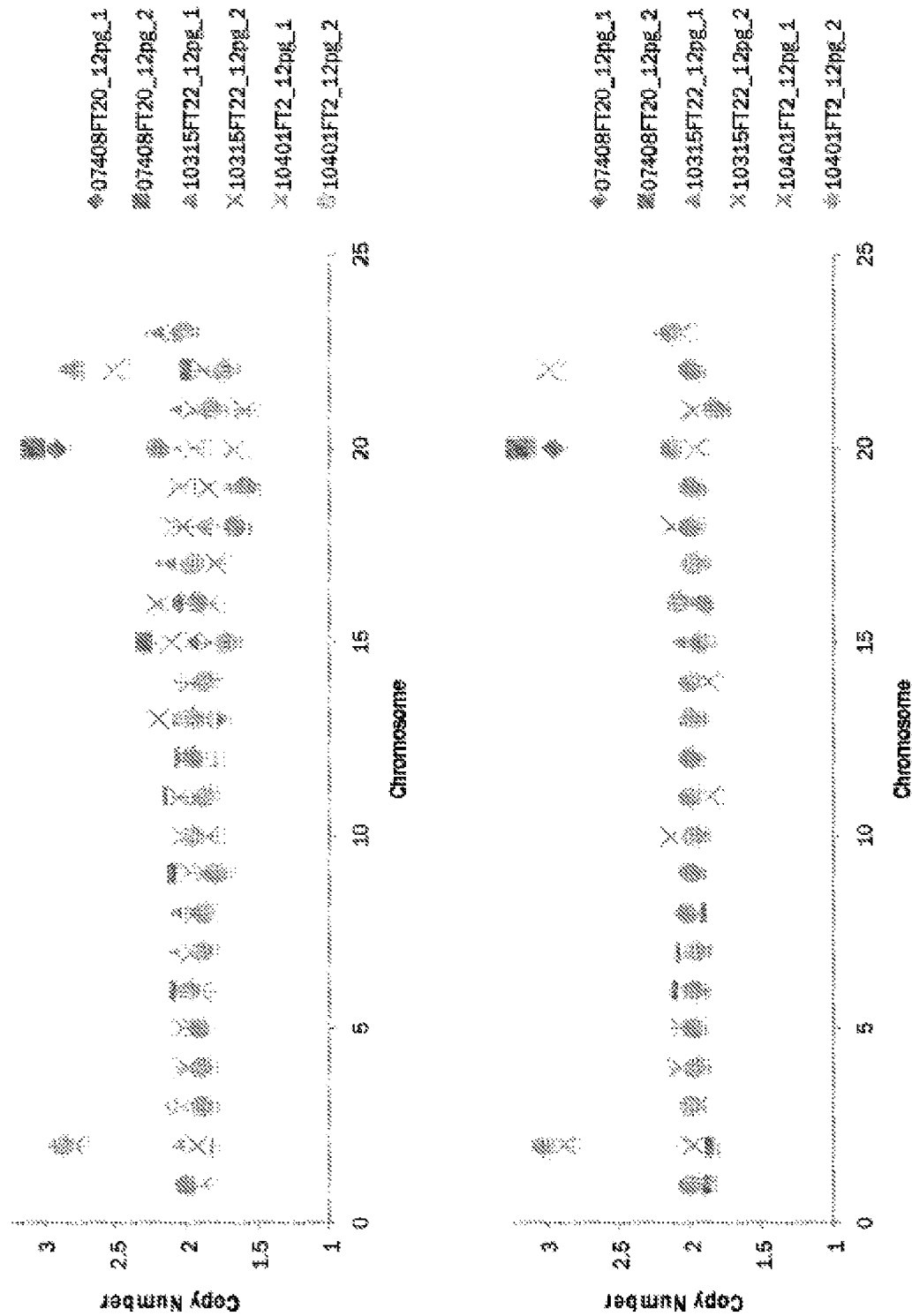
FIG. 3 shows the effect of rescaling and normalization. Rescaling chromosomal read fractions based on DNA content and performing quantile normalization based on the newly calculable read fractions per individual chromosome greatly decreases data noise and allows accurate identification of copy number variation. For example, in the absence of rescaling, the copy numbers for the trisomy 2 sample (gray circles) are all significantly less than the expected integer values; after rescaling, the values all shift much closer to whole number chromosome counts.

The algorithm of the present invention leads to an improvement in the accuracy of chromosomal copy number determination with greatly reduced noise and fewer chromosomes falsely being identified as having abnormal copy numbers. The results of employing the algorithm discussed herein are shown in FIG. 3. FIG. 3 shows the rescaling chromosomal read fractions based on DNA content with quantile normalization based on the newly calculable read fractions per individual chromosome. The results show a great decrease in data noise, which allows for accurate identification of copy number. As shown in FIG. 3, for example, in the absence of rescaling, the copy numbers for the trisomy 2 sample in the top graph (orange circles) are all significantly less than the expected integer values. After rescaling, as shown in the bottom graph, the values all shift much closer to whole number chromosome counts.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed:

1. A method for determining copy number states of chromosomes in a sample, the method comprising the steps of:

extracting DNA from an embryo-derived sample suspected to include at least one chromosome with an altered copy number;

sequencing the DNA to generate sequence reads, wherein sequencing includes fragmenting the DNA into sequences of at least 300 base pairs to generate the sequence reads;

obtaining read counts as a number of the sequence reads that map to each chromosome;

calculating chromosomal read fractions as the fraction per chromosome of a total of the read counts;

correcting an error caused by interdependence in the chromosomal read fractions by multiplying each chromosomal read fraction by a scaling factor that arithmetically minimizes a sum of distances between the read fractions and respective nearest whole number multiples of control euploid read fractions to obtain scaled read fractions;

normalizing the scaled read fractions by estimating the exact number of each chromosome in a given sample; and calling a copy number for the embryo-derived sample using the normalized scaled read fractions from each chromosome.

2. The method of claim 1, further comprising determining a copy number state for each chromosome.

3. The method of claim 1, further comprising the step of diagnosing embryonic aneuploidy.

4. The method of claim 1, further comprising the step of diagnosing fetal aneuploidy.

5. The method of claim 1, wherein the sequencing comprises a next-generation sequencing method or a FAST-SeqS sequencing method.

6. The method according to claim 1, wherein the sample comprises blood or plasma.

7. The method of claim 1, further comprising the step of diagnosing tumor cell aneuploidy.

8. The method of claim 1, wherein sequencing comprises a next-generation sequencing method.

9. The method of claim 1, wherein the sample comprises blood.

10. The method of claim 1, wherein the sample is at least one of: skin tissue, endometrial tissue, trophectoderm biopsy-derived tissue, nasal passage tissue, CNS tissue, neural tissue, eye tissue, liver tissue, kidney tissue, mammary gland tissue, placental tissue, gastrointestinal tissue, musculoskeletal tissue, genitourinary tissue, or bone marrow.

11. The method of claim 1, further comprising isolating the DNA.

* * * * *